United States Patent
Brugnara et al.

(12)

(10) Patent No.: US 6,331,557 B1
(45) Date of Patent: Dec. 18, 2001

(54) USE OF DIVALENT CATIONS FOR INHIBITING ERYTHROCYTE DEHYDRATION IN VIVO

(75) Inventors: Carlo Brugnara, Newton Highlands, MA (US); Yves Beuzard, Paris; Frederick Galacteros, Cretgil, both of (FR); Lucia De Francheschi, Verona (IT)

(73) Assignees: Children's Medical Center Corporation, Boston, MA (US); Insitut National de la Sante et de la Reicherche Medicale (Inserm), Cedex; Establissement Public Assistance Publique Hopitaux de Paris, Paris, both of (FR)

( * ) Notice: Subject to any disclaimer, the term of this patent is extended or adjusted under 35 U.S.C. 154(b) by 0 days.

(21) Appl. No.: 09/530,710

(22) Filed: Nov. 9, 2000

Related U.S. Application Data

(60) Provisional application No. 60/064,896, filed on Nov. 7, 1997.

(51) Int. Cl.[7] ................................................. A61K 31/40
(52) U.S. Cl. ................................................. 514/423
(58) Field of Search ............................................. 514/423

(56) References Cited

U.S. PATENT DOCUMENTS 5,441,957 * 8/1995 Brugnara et al. ..................... 514/252

OTHER PUBLICATIONS

De Franceschi, et al., J. Clin. Invest. 100:1847–1852, 1997.*

Brugnara Current Opinion in Hematology, 2:132–138, 1995.*

Bridges et al. Blood, vol. 88, No. 12; pp. 4701–4710, 1996.*

Goldberg et al., Seminars in Oncology, vol. 19, No. 3, Suppl. 9, pp. 74–81, 1992.*

* cited by examiner

*Primary Examiner*—Raymond Henley, III
(74) *Attorney, Agent, or Firm*—Wolf, Greenfield & Sacks, P.C.

(57) ABSTRACT

The present invention provides a chemical class of active agents to be used as efficacious drugs in preventing erythrocyte dehydration, thus helping ameliorate the symptoms of certain hemoglobinopathies. The active agents include a class of compounds that can deliver to an erythrocyte in vivo a divalent cation. Increased intracellular concentrations of the divalent cation in the erythrocyte block K—Cl cotransport preventing dehydration of the erythrocyte, thus improving erythrocyte survival. These agents are to be administered by any preferred route of administration including oral, intravenous and parenteral routes. These agents may be co-administered with any other anti-hemoglobinopathic compounds. The methodology is effective for both long term and short term therapy; may be employed prophylactically and/or therapeutically; and may be used in acute crisis clinical situations.

52 Claims, 4 Drawing Sheets

USE OF DIVALENT CATIONS FOR INHIBITING ERYTHROCYTE DEHYDRATION IN VIVO

RELATED APPLICATIONS

This application is the National Stage of International Application No. PCT/US98/23622, filed Nov. 6, 1998, which claims priority to U.S. Provisional patent application Ser. No. 60/064,896, filed Nov. 7, 1997, entitled "USE OF DIVALENT CATIONS FOR INHIBITING ERYTHROCYTE DEHYDRATION IN VIVO," the entire contents of which are incorporated herein by reference.

GOVERNMENT SUPPORT

The work resulting in this invention was supported in part by NIH Grant Nos. RO1DK50422 and P60-HL15157, and General Clinical Research Grant No. M01-RR02172. The U.S. Government may therefore be entitled to certain rights in the invention.

FIELD OF THE INVENTION

The present invention is concerned with effective treatments for hemoglobinopathies and the clinical pathologies and manifestations resulting thereby. This invention is particularly concerned with effective treatments for inhibiting dehydration in an erythrocyte cell and delaying the occurrence of erythrocyte cell deformation in the microcirculation of a hemoglobinopathic human.

BACKGROUND OF THE INVENTION

Although sickle cell disease and its clinical manifestations has been recognized within West Africa for several centuries, the first report of sickle cell anemia appearing in the medical literature occurred only in 1910 when James B. Herrick documented the presence of anemia in a 20-year old black male using photomicrographs illustrating the presence of "thin sickle-shaped and crescent-shaped" red cells (*Arch. Intern. Med.*, 1910, 6: 517). Other cases of sickle cell disease were then continually recognized and reported over the next forty years until when in 1949 it was unequivocally confirmed that patients with sickle cell anemia had an electrophoretically abnormal hemoglobin, whereas those with the "sickle trait" had equal amounts of the normal and abnormal hemoglobin components. (Pauling, L., et al., *Science*, 1949, 110:543–548). The inheritance pattern of other hemoglobin variants was subsequently clarified and provided convincing evidence that hemoglobin (Hb) S and hemoglobin (Hb) C are allelic variants of normal hemoglobin.

Sickle cell anemia and the existence of sickle hemoglobin (Hb S) was the first genetic disease to be understood at the molecular level; and is recognized today as the morphological and clinical result of the glycine to valine substitution at the No. 6 position of the beta globin chain (Ingram, V M, *Nature*, 1956, 178:792–794). The origin of the amino acid change and of the disease state is the consequence of a single nucleotide substitution (Marotta et al, *J. Biol. Chem.*, 1977, 252:5040–5053).

As sickle cell disease became better known and more easily identified, a remarkable degree of clinical heterogeneity in the physical manifestations and symptoms of sickle cell disease has become recognized. The anemia typically is of moderate severity and is usually well compensated by the dynamic steady state systems. The major source of mobidity and mortality is vaso-occlusion-which causes repeated episodes of pain in both acute and chronic form and also causes ongoing organ damage with the passage of time. Vascular occlusion often results in infarction of bone and/or bone marrow. Pulmonary and renal damage are frequently lethal in young adults; and cerebral infarction is often debilitating or fatal in children. Typically, patients afflicted with sickle cell disease are also very susceptible to bacterial infections and splenic dysfunction. Publications which describe the clinical and pathological manifestations in detail and review sickle cell disease are represented by the following: Clinton H. Joiner, Cation Transport And Volume Regulation In Sickle Red Blood Cells, American Journal of Physiology, 1992; Bunn, H F, and B. G. FoRget, *Hemoglobin: Molecular, Genetic and Clinical Aspects*, W. B. Saunders Co., Philadelphia, 1986, Chapters 11 and 12, pp. 453–564; Eaton, W A and Hofrichter, *J., Blood*, 1987, 70:1245–1266); and Hebbel, R P, *Blood*, 1991, 77:214–237); and the references cited within each of these publications.

It has long been recognized and accepted that the deformation and distortion of sickle cell erythrocytes upon complete deoxygenation is caused by polymerization and gelation of hemoglobin S. The phenomenon is well reviewed and discussed by Eaton and Hofrichter, *Blood*, 1987, 70:1245). To gain some perspective on the problem and consequences of Hb S polymerization and intracellular gelation, it is useful to consider the events believed to occur as a red cell travels through the circulation of a patient afflicted with sickle cell disease. Erythrocytes containing no polymerized hemoglobin S in the arterial circulation may pass through the microcirculation and return to the lungs without sickling; or they may sickle in the veins; or they may sickle in the capillaries. For purposes of description, sickling is equivalent with intracellular gelation. The probability for each of these possible events for the sickle red cell will be determined by the delay time for intracellular gelation relative to the appropriate capillary transit time (Eaton, W A, et al., *Blood*, 1976, 47:621). Thus, if it is thermo-dynamically impossible for intracellular gelation to take place, or if the delay time at venous oxygen pressures is longer than about 15 seconds, then cell sickling will not occur. Alternatively, if the delay time is between about 1 and 15 seconds, then the red cell will likely sickle in the veins. However, if the delay time is less than about 1 second, the red cell will sickle within the capillaries.

Note that for red cells that sickle within the capillaries, a number of possibilities exist as the consequent events-ranging from no effect on its transit time, to transient occlusion of the capillary, or to a more permanent blockage that may ultimately result in ischemia, or the infarction of the surrounding cells, and in destruction of the red cell. Which of these various possibilities and differing events will actually occur will depend on a number of factors: the total intracellular hemoglobin concentration; the composition of the intracellular hemoglobin; the rate and extent of deoxygenation; and the various transit times involved for the cells.

In addition, for unsickled red cells entering the microcirculation, a long capillary transit time will increase the probability of the potentially damaging vaso-occlusive events in two different ways. First, it will permit increased oxygen extraction which, in turn, will shorten the delay time. Second, it will increase the probability that a red cell with a given delay time will sickle within the capillary. Thus, for cells that either enter the microcirculation already sickled or become sickled within the microcirculation, there is a clear probability for occlusion of the small vessels; and the duration of an occlusion may be sufficiently long to comprise the oxygen supply to the surrounding tissues and hence alter the sickling a consequent vaso-occlusion in nearby microvessels. It is therefore critically important to recognize that vaso-occlusion is a dynamic process in which the fraction of capillaries that are occluded depends upon both rates of occlusion and the rate of capillary reopening. The factors that influence the transit times and the duration of occlusions thus play a critical role in the pathology in the sickle cell disease state.

It will also be noted and appreciated that the physical manifestations of sickle cell disease are paralleled by a cellular pathophysiology which is markedly diverse and varied. Certainly, much of the physiological dysfunction in sickle erythrocytes arises from the tendency of deoxy hemoglobin S to form an intracellular polymer-which results in a marked increase in cellular viscosity and impairment of rheological function. Sickle cells exhibit oxidative damage; abnormal adherence to endothelial cells, monocytes and other red cells; increased membrane rigidity; abnormal cytoskeleton function; deranged lipid structure; cation deletion and cellular dehydration; and abnormal carrier-mediated and passive permeability to cations.

Knowledge of the pathophysiology of sickle cell disease is merely one aspect of the continuing research interest in the physiology of erythrocyte cells generally. Considerable investigative efforts have focused upon the mechanisms of action and the various systems responsible for cation transport and volume regulation in normal red blood cells. In particular, the potassium transport pathways and the consequences of erythrocyte dehydration have been of major interest. A current summary of the various potassium transport pathways present in normal human erythrocytes is given by Table A below.

stantial rheological consequences. Thus, the physiological mechanisms that maintain the water content of normal erythrocyte cells, and the pathological conditions that cause loss of water from erythrocyte cells in the blood circulation, are critically important. Moreover, since cell water will follow osmotically any change in the intracellular concentration of ions, the maintenance of the red cell's potassium concentration is of particular importance (Stuart, J., and Ellory, J C, *Brit. J. Haematol.*, 1988, 69:1–4).

U.S. Pat. Nos. 5,273,992 and 5,441,957 describe the use of imidazoles, nitroimidazoles, triazoles and other aromatic compounds used in blocking of the Gardos channel, thus inhibiting the loss of K and preventing dehydration. The other major pathway responsible for the transport of K involves the K—Cl cotransporter system. The K—Cl cotransport system promotes loss of K and Cl with consequent erythrocyte dehydration when the cells are exposed to pH values lower than 7.4 (Brugnara, C., et al., *J. Clin. Invest.*, 1985, 75: 1608–1617). To date, there exist no pharmacological inhibitors of this pathway that can be used to prevent cell dehydration. However, K—Cl cotransport is exquisitely sensitive to cell magnesium (Mg) concentration as well as other divalent cations, and a modest increase in cell Mg and/or other divalent cations induces marked inhibition of K—Cl cotransport in vitro (Brugnara, C., and Tosteson, D C, *Blood.*, 1987, 70: 1810–1815). The Mg content of the red blood cell is an essential modulator of red blood cell volume, volume regulatory mechanisms, and enzymes involved in essential cellular metabolic functions. Erythrocyte Mg content also affects the activity of various membrane cation transport pathways such as the Na/K pump, Na—K—Cl cotransport, Ca and K channels, and

TABLE A

Potassium Transport Pathways in Human Erythrocytes*
Maximal Capacity as K+ transporter

| System | Mode | (mmol/l.cells/h) | Inhibitor | Comments | Reference |
|---|---|---|---|---|---|
| NA+/K+ pump | Normally 3NA + 2K+ but partial fluxes occur | 1–3 | Cardiac glycosides (ouabain) | ATP-driven: operates at approx. 50% $V_{max}$ at normal cell [Na+] | Glynn, L M, The Enzymes of Biological Membranes. 1985. |
| NaKCl contransport | 1Na+:1K+:2C 1-complex partial and exchange fluxes | 0.1–1.5 | Loop diuretics (bumetanide, furosemide) | Poised at close to equilibrium (i.e., zero net fluxes under physiological conditions) | Chipperfield, AR, Clin. Sci. 71:465 (1986). |
| KCl cotransport | 1K+:Cl– | >10 | Internal divalent cations; loop diuretics at high concentrations | Highest in young cells; activated by NEM, pressure, cell swelling, acid pH. | Ellory, et al. Biomed. Biochem. Acts 46:531 (1987). |
| $Ca^{2+}$-activated K+ channel (Gardos channel) | Uncoupled K+ | >10 | Quinine | Activated by raised cell $[Ca^{2+}]$ | Lew & Ferreira Cur. Top. Memb. Transp. 10:217 (1978). |

*Source: Stuart, J. and J. C. Ellory, Brit. J. Haematol. 69:1–4 (1988).

It has long been recognized that cytoplasm of the normal erythrocyte comprises approximately 70% water. Water crosses a normal erythrocyte membrane in milliseconds; however, the loss of cell water causes an exponential increase in cytoplasmic viscosity as the mean cell hemoglobin concentration (MCHC) rises above about 32 g/dl. Since cytoplasmic viscosity is a major determinate of erythrocyte deformability, the dehydration of the erythrocyte has sub- K—Cl cotransport, and cell membrane structure and function. When Mg is increased, Cl moves into the cell to compensate the positively charged Mg ions with osmotically obligated water influx and consequent cell swelling.

A recent study using a transgenic mouse model for sickle cell disease (SAD 1 mouse, Trudel, M., et al., *EMBO J.*, 1991, 11: 3157–3165), showed that a Mg-deficient diet led to worsening anemia, reticulocytosis, and increased dehydration of SAD 1 mouse red blood cells. By contrast, a high Mg-diet decreased K—Cl cotransport activity, red blood cell dehydration, and K loss of transgenic SAD 1 mouse red blood cells, and more importantly increased Hb levels, suggesting a possible amelioration of the disease (De Franceschi, L., et al., *Blood*, 1996, 88: 2738–2744).

In human patients, Mg supplements have been used to improve glucose oxidation in elderly, noninsulin-dependent (type II) diabetics (Paolisso, G., et al., *J. Clin. Endocrinol. Metab.*, 1994,78: 1510–1514; Paolisso, G.,et al.,*Am. J Clin. Nutr.*, 1992,55: 1161–1167). Several uncontrolled studies that had focused on possible hemodynamic and vascular effects of various Mg preparations have been conflicting as to the benefits of Mg supplementation therapy in SS disease patients. Although initial reports indicated that orally or intravenously administered magnesium such as Mg citrate or Mg sulfate might be therapeutically beneficial for treating subjects with SS disease, subsequent studies have demonstrated that the therapeutic administration of Mg did not improve erythrocyte cell survival. (Anstall, H B, et al., *Lancet*, 1959, 1: 814–815; Lehmann, H., *Br. Med J.*, 1963, 1: 1158–1159). For instance, a 7-day course of oral Mg supplementation using Mg citrate did not change erythrocyte survival in three patients with SS disease (Basu, A K, and Woodruff, A W, *Trans. R. Soc. Trop. Med. Hyg.*, 1966, 60: 64–69). More recently, our own experiments showed no clinical benefits to sickle cell patients by the administration of Mg lactate (Brugnara, C., et al., unpublished observations).

Therefore, there exists a longstanding and well recognized need for an effective method of treating erythrocyte cell deformation in vivo, and in particular erythrocyte cells of subjects with a hemoglobinopathy such as sickle cell disease and thalassemia.

SUMMARY OF THE INVENTION

It has been discovered that certain compounds described herein improve hemoglobinopathic conditions.

The present invention involves the unexpected finding that a certain class of K—Cl cotransport inhibitor molecules exert their effect in hemoglobinopathic erythrocyte cells in vivo, helping ameliorate the detrimental effects of hemoglobinopathies such as sickle cell anemia and the thalassemias, improving dramatically the lifestyles of patients.

According to one aspect of the invention, a method for inhibiting erythrocyte cell dehydration in a subject is provided. The method involves administering to a subject in need of such treatment, a pharmaceutically acceptable agent that blocks in a subject K—Cl cotransport in erythrocytes of the subject, in an amount effective to inhibit erythrocyte cell dehydration in the subject In one embodiment, the compounds useful in the invention have the general formula:

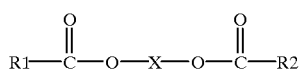
(I)

wherein X is a divalent cation selected from the group consisting of Mg, Ca, Mn, Sr and Zn; and wherein R1 and R2 each is an aryl group or a heteroaryl group. Heteroaryl groups may include for instance atoms such as oxygen, nitrogen or sulfur. Such aryl groups or heteroaryl groups can be unsubstituted, or substituted with substituents selected from the group consisting of $(C_1-C_6)$ alkyl, $(C_1-C_6)$ alkenyl and $(C_1C_6)$ alkynyl, —CN, —OR', —SR', —NO$_2$, —NR'R', halogen, amino acid, —R", —C(O)R", —C(S)R", —C(O)OR", —C(S)OR", —C(O)SR", —C(S)SR", —C(O)N(R')$_2$, —C(O)C(O)R', —C(S)C(O)R", —C(O)C(S)R", —C(S)C(S)R", —C(O)C(O)OR", —C(S)C(O)OR", —C(O)C(S)OR", —C(O)C(O)S R", —C(S)C(S)OR", —C(S)C(O)SR", —C(O)C(S)SR", —C(S)C(S)SR", —C(O)C(O)N(R")$_2$, —C(S)C(O)N(R")$_2$, —C(O)C(S)N(R")$_2$, or —C(S)C(S)N (R")$_2$, wherein each R' is independently selected from the group consisting of —H, $(C_1-C_6)$ alkyl, $(C_1-C_6)$ alkenyl and $(C_1-C_6)$ alkynyl, and wherein each R" is independently selected from the group consisting of —H, $(C_1-C_6)$ alkyl, $(C_1-C_6)$ alkenyl, $(C_1-C_6)$ alkynyl, $(C_6-C_{20})$ aryl, $(C_6-C_{20})$ substituted aryl, $(C_6-C_{26})$ alkaryl and substituted $(C_6-C_{26})$ alkaryl, and the aryl and alkaryl substituents are each independently selected from the group consisting of —CN, —OR', —SR', —NO$_2$, —NR'R', halogen, $(C_1-C_6)$ alkyl, $(C_1-C_6)$ alkenyl, $(C_1-C_6)$ alkynyl and trihalomethyl.

In one important embodiment of the invention, R1 and R2 are each a 2-pyrrolidone, and the divalent cation X is Mg. This preferred compound of the invention has the formula:

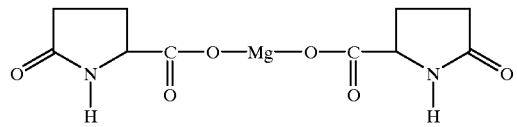

In an embodiment of the invention, the compounds may be administered in combination with an anti-hemoglobinopathic agent, other than a pharmaceutically acceptable agent that blocks in a subject K—Cl cotransport inerythrocytes of a subject. In a preferred embodiment of the invention the anti-hemoglobinopathic agent is selected from the group consisting of an erythrocyte cell dehydration inhibitor, a sickle hemoglobin inhibitor, an agent that increases fetal hemoglobin production and an agent that increases microvascular blood flow.

According to one embodiment of the invention, the subject who is in need of such treatment is a patient with sickle cell disease. Preferably the patient with sickle cell disease is administered the compound of the invention orally, parenterally, or by intravenous administration. In another embodiment of the invention, the subject who is in need of such treatment is a patient with a thalassemia Preferably the patient with thalassemia is administered the compound of the invention orally, parenterally, or by intravenous administration.

The invention also provides methods for inhibiting erythrocyte cell dehydration in vitro. The method involves contacting an erythrocyte cell that has been isolated from a subject with an agent that blocks K—Cl cotransport in an erythrocyte, in an amount effective to inhibit erythrocyte cell dehydration, the agent having the general formula:

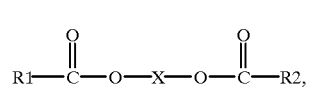
(I)

with substituents as described above.

In a preferred embodiment at least one of R1 and R2 is 2-pyrrolidone.

In one important embodiment of the invention, R1 and R2 are each a 2-pyrrolidone, and the divalent cation X is Mg. This preferred compound of the invention has the formula:

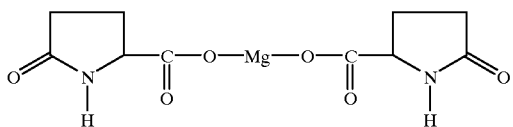

In an embodiment of the invention, the compounds are contacted with an erythrocyte cell in vitro in combination with an anti-hemoglobinopathic agent other than the compounds of Formula I. In a preferred embodiment of the invention the anti-hemoglobinopathic agent is selected from the group consisting of an erythrocyte cell dehydration inhibitor, a sickle hemoglobin inhibitor, an agent that increases fetal hemoglobin production and an agent that increases microvascular blood flow.

According to another aspect of the invention, pharmaceutical preparations are provided. In one aspect the pharmaceutical preparation is a pharmaceutical composition including a pharmaceutically acceptable agent that blocks K—Cl cotransport in an erythrocyte of a subject, an anti-hemoglobinopathic agent other than an agent that blocks K—Cl cotransport in an erythrocyte of a subject, and a pharmaceutically acceptable carrier. In one embodiment the agent that blocks K—Cl cotransport has the general formula:

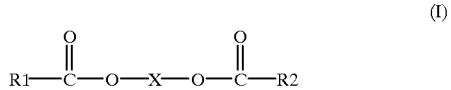

(I)

with substituents as described above.

In a preferred embodiment at least one of R1 and R2 is 2-pyrrolidone.

In one important aspect of the invention, R1 and R are each a 2-pyrrolidone, and the divalent cation X is Mg. This preferred compound of the invention has the formula:

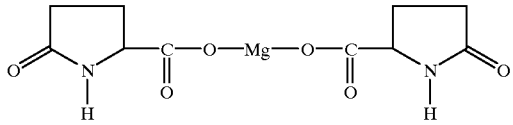

In a preferred pharmaceutical composition the anti-hemoglobinopathic agent is selected from the group consisting of an erythrocyte cell dehydration inhibitor, a sickle hemoglobin inhibitor, an agent that increases fetal hemoglobin production and an agent that increases microvascular blood flow.

In an important embodiment of the invention, the pharmaceutical carrier used is a comestible product.

The foregoing pharmaceutical compositions can be administered in effective amounts to subjects suffering from a hemoglobinopathy.

In another aspect of the invention the compounds described earlier are packaged in a kit. The kit of the invention is a package housing: i) a container containing a pharmaceutically acceptable agent that blocks in a subject K—Cl cotransport in erythrocytes of a subject, in amounts effective to inhibit erythrocyte cell dehydration in a subject, and ii) instructions for using said agent to treat erythrocyte cell dehydration, in a subject in need of such treatment. The agent preferably is a compound described by Formula I with substituents and preferred compounds as described above. In one embodiment of this invention the kit further includes a container containing an anti-hemoglobinopathic agent other than said agent that blocks K—Cl cotransport in erythrocytes of the subject. A preferred anti-hemoglobinopathic agent is selected from the group consisting of an erythrocyte cell dehydration inhibitor, a sickle hemoglobin inhibitor, an agent that increases fetal hemoglobin production and an agent that increases microvascular blood flow. A preferred kit of the invention includes the preferred compound of the invention, Mg pidolate.

A further aspect of the invention involves the compounds of the invention as described earlier by general formula (I), and anti-hemoglobinopathic agents other than said agent that blocks in a subject K—Cl cotransport in erythrocytes of the subject, packaged together in a kit. Such kit includes i) a first container containing a pharmaceutically acceptable agent that blocks in a subject K—Cl cotransport in erythrocytes of the subject, ii) a second container containing an anti-hemoglobinopathic agent other than said agent that blocks in a subject K—Cl cotransport in erythrocytes of the subject, and iii) instructions for using said agents to treat hemoglobinopathies. A preferred anti-hemoglobinopathic agent is selected from the group consisting of an erythrocyte cell dehydration inhibitor, a sickle hemoglobin inhibitor, an agent that increases fetal hemoglobin production and an agent that increases microvascular blood flow. A preferred kit of the invention includes the preferred compound of the invention, Mg pidolate.

These and other aspects of the invention will be described in greater detail below.

DETAILED DESCRIPTION OF THE INVENTION

Figure 1:
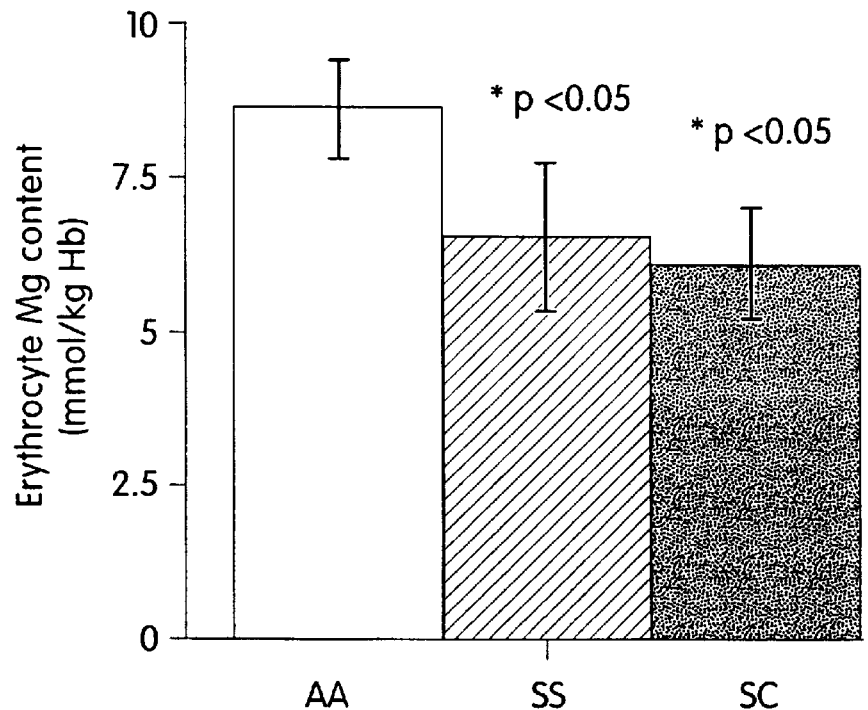
FIG. 1 shows erythrocyte Mg content in normal controls and in untransfused patients with SS and SC disease.

The invention is useful whenever it is desirable to inhibit dehydration in an erythrocyte cell such as in the treatment of a hemoglobinopathy.

The invention includes a method for inhibiting dehydration of erythrocytes in a subject by administering to the subject a pharmaceutically acceptable agent that blocks K—Cl cotransport in the erythrocytes of the subject. The invention also includes a method for inhibiting dehydration of erythrocytes in vitro, accomplished using the aforementioned agent.

Additionally, the invention includes a pharmaceutical preparation including a pharmaceutically acceptable agent that blocks K—Cl cotransport in erythrocytes and an anti-hemoglobinopathic agent. Kits containing preparations are also part of the present invention.

A "pharmaceutically acceptable agent that blocks in a subject K—Cl cotransport" as used herein is a compound that inhibits K—Cl cotransport in an erythrocyte cell in vivo. It is believed that this occurs by raising the cell's intracellular concentration of a divalent cation. Such increase in the intracellular concentration of a divalent cation is believed to result in blocking of the K—Cl cotransport system which in turn leads to an osmotic water retention by the cell (inhibiting dehydration), and to cell swelling. Although inhibitors of K—Cl cotransport are known in the art, "agents that block in a subject K—Cl cotransport" as used herein refer only to compounds which block K—Cl cotransport in vivo. It has been discovered that the compounds in the prior art which are known to be effective for inhibiting K—Cl cotransport in vitro are ineffective in vivo. Thus, an aspect of the invention is to use in vivo screening to determine whether a compound useful in vivo has utility in vivo. Following such procedures, applicants have discovered compounds that are effective in vivo.

A simple method for assaying changes in intracellular concentrations of at least one type of a divalent cation (and thus inhibition of dehydration) is measuring the swelling of the erythrocyte cell. Such measurement can be accomplished using a Technicon H*3 Hematology analyzer (Bayer Corp., Diagnostics Division, Tarrytown, N.Y.) to measure, amongst other parameters, erythrocyte volume.

In addition to this assay other cellular parameters are useful for assessing whether a particular compound is useful for blocking K—Cl cotransport in vivo and/or erythrocyte dehydration. One direct way is to measure the K—Cl cotransport from erythrocytes isolated from a human subject, as net K$^+$ efflux into hypotonic medium. Another way is to directly measure the K$^+$ and Na$^+$ content of isolated erythrocytes using atomic absorption spectrometry. Another indirect way is to quantitate cellular deformability of an erythrocyte using osmotic gradient ektacytometry. Cellular deformability is regulated by surface area, surface area-to-volume ratio, and the state of hydration in the erythrocyte cell. All of the foregoing measurements can be compared to controls, and all of the foregoing techniques are well known to those of ordinary skill in the art, and some are described in the examples below.

A preferred "agent that blocks in a subject K—Cl cotransport" of the present invention is an agent having a structure of the following general formula (I):

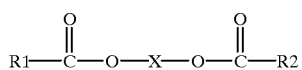

(I)

wherein X is a divalent cation selected from the group consisting of Mg, Ca, Mn, Sr and Zn; and
wherein R1 and R2 each is an aryl group or a heteroaryl group. Heteroaryl groups may include for instance atoms such as oxygen, nitrogen or sulfur. Such aryl groups or heteroaryl groups can be unsubstituted, or substituted with substituents selected from the group consisting of $(C_1-C_6)$ alkyl, $(C_1-C_6)$ alkenyl and $(C_1-C_6)$ alkynyl, —CN, —OR', —SR', —NO$_2$, —NR'R', halogen, amino acid, —R", —C(O)R", —C(S)R", —C(O)OR", —C(S)OR", —C(O)SR", —C(S)SR", —C(O)N(R")$_2$, —C(O)C(O)R", —C(S)C(O)R", —C(O)C(S)R", —C(S)C(S)R", —C(O)C(O)OR", —C(S)C(O)OR", —C(O)C(S)OR", —C(O)C(O)SR", —C(S)C(S)OR",—C(S)C(O)SR",—C(O)C(S)SR",—C(S)C(S)SR", —C(O)C(O)N(R")$_2$, —C(S)C(O)N(R")$_2$, —C(O)C(S)N(R")$_2$, or —C(S)C(S)N(IV)$_2$, wherein each R' is independently selected from the group consisting of —H, $(C_1-C_6)$ alkyl, $(C_1-C_6)$ alkenyl and $(C_1-C_6)$ alkynyl, and wherein each R" is independently selected from the group consisting of —H, $(C_1-C_6)$ alkyl, $(C_1-C_6)$ alkenyl, $(C_1-C_6)$ alkynyl, $(C_6-C_{20})$ aryl, $(C_6-C_{20})$ substituted aryl, $(C_6-C_{26})$ alkaryl and substituted $(C_6-C_{26})$ alkaryl, and the aryl and alkaryl substituents are each independently selected from the group consisting of —CN, —OR', —SR', —NO$_2$, —NR'R', halogen, $(C_1-C_6)$ alkyl, $(C_1-C_6)$ alkenyl, $(C_1-C_6)$ alkynyl and trihalomethyl.

In a preferred embodiment R1 and R2 each are the same compound which is 2-pyrrolidone.

In another preferred embodiment the divalent cation X is magnesium (Mg).

According to the invention, a preferred compound is magnesium pidolate (magnesium pyrrolidone carboxylate, or magnesium pyroglutamate) of the formula:

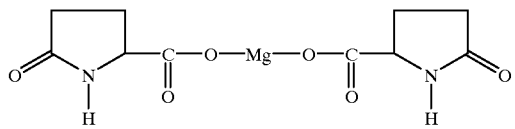

The compounds of general formula (I) of the invention are derived from commercially available compounds or are synthesized de novo using routine chemical synthetic procedures known to those of ordinary skill in the art. The preferred compound of the invention is commercially available, and has been used safely in humans.

The present invention is useful whenever it is desirable to reduce erythrocyte dehydration. It is particularly useful for delaying the occurrence of erythrocyte distortion in situ, and desirably in the microcirculation of a human afflicted with a hemoglobinopathy. "Hemoglobinopathies" as used herein, fall into one of three classes of disorders: i) Structural hemoglobinopathies, in which the hemoglobins have altered amino acid sequences resulting in their deranged function or altered physical or chemical properties; examples include abnormal hemoglobin polymerization (sickle cell anemia, Hb-S), altered O$_2$, affinity (high affinity-polycythemia, low affinity-cyanosis, pseudoanemia), hemoglobins that oxidize readily, unstable hemoglobins, hemolytic anemia, jaundice, M-hemnoglobins (methemoglobinemia. cyanosis); ii) Thalassemias, in which there is defective production of globin chains; examples include a-thalassemias, b-thalassemias, and db-, gdb-, ab-thalassemias; and iii) Structural hemoglobinopathies in which structurally abnormal hemoglobin is associated with co-inherited thalassemias; examples include Hb E, Hb Constant Spring, Hb Lepore.

A "subject" as used herein is a human.

The methods and products of the invention are preferably useful, inter alia, whenever it is desirable to diminish the time and duration of erythrocyte cell sickling and vaso-occlusion in the blood circulation. This includes treating sickle cell disease prophylactically to decrease hemoglobin-S concentration and prevent sickling, as well as therapeutically treating patients with acute sickle cell crisis by intramuscular or intravenous administration. The invention may also be used for the treatment of chronic sickle cell episodes for example to control the frequency and/or duration of the episodes.

The methods and products of the invention are also useful, inter alia, whenever it is desirable to improve erythrocyte cell condition and/or survival in a subject with thalassemia. Conventional assays can be used to evaluate a subjects erythrocytes as known by those skilled in this art. In addition, an indirect measurement can be made by the measurement of the absolute number of reticulocytes in a thalassemic subject before and after treatment. For example, a measurement is made at the onset of treatment, and then a measurement is made 8-weeks from the onset of treatment of a thalassemic subject. A decrease in the absolute number of reticulocytes in the subject receiving such treatment is indicative of improvement in the subject's condition.

Important embodiments of the invention involve the co-administration of anti-hemoglobinopathic agents that are non-K—Cl cotransport inhibitors but that can act cooperatively, additively or synergistically with agents that block K—Cl cotransport to further improve the treatment of hemoglobinopathic disorders. Thus, other anti-hemoglobinopathic agents (non-K—Cl cotransport inhibitors) can be co-administered with the agents that block K—Cl cotransport according to the invention. Such anti-hemoglobinopathic agents include those falling into one of four categories of compounds, each of which is well known in the art, according to the effects they exert.

One category of anti-hemoglobinopathic agents include compounds which inhibit erythrocyte dehydration. Such compounds are described, for example, in U.S. Pat. Nos. 5,273,992 and 5,441,957, the entire disclosures of which are incorporated herein by reference. The '992 and '957 patents describe the use of imidazoles, nitroimidazoles, triazoles and other aromatic compounds used in blocking of the Gardos channel of an erythrocyte, thus preventing erythrocyte cell dehydration. Another example includes the agent dipyridamole. Dipyridamole has been shown to prevent erythrocyte dehydration by inhibiting the oxygenation induced cation fluxes.

Another category of anti-hemoglobinopathic agents inhibit Hb-S polymerization. An example of such compound includes Nitric Oxide. Low concentrations of Nitric Oxide have been shown to increase the affinity of Hb-S for Oxygen, thus preventing Hb-S polymerization.

A third category of anti-hemoglobinopathic agents increase fetal hemoglobin (Hb-F) levels. An example of such agent includes hydroxyurea (HU), an inhibitor of DNA synthesis, which has been shown to increase the cellular concentration of fetal hemoglobin, reducing the cellular levels of Hb-S, or chemically modifying Hb-S.

The last category of anti-hemoglobinopathic agents increase microvascular blood flow. An example of such agent includes RheothRx (Poloxamer 188-Glaxo Wellcome, Inc., Res. Triangle Park, N.C.). Since the painful episodes at the end of organ damage usually associated with sickle cell disease are caused by microvascular occlusion and tissue ischemia resulting from complex interactions between the sickle erythrocytes, endothelium, platelets, etc., an agent that improves microvascular flow can significantly improve the condition.

The agent that blocks K—Cl cotransport and the anti-hemoglobinopathic agent may be administered together in a common administration vehicle (e.g., pill, tablet, implant, injectable solution, etc.) This vehicle would contain both the pharmaceutically acceptable agent that blocks K—Cl cotransport in erythrocytes and the anti-hemoglobinopathic agent, with or without pharmaceutically acceptable carriers. Alternatively, the K—Cl cotransport inhibitor is administered substantially simultaneously with the anti-hemoglobinopathic agent. By substantially simultaneously, it is meant that the K—Cl cotransport inhibitor is administered to the subject close enough in time with the administration of the anti-hemoglobinopathic agent (non-K—Cl cotransport inhibitor), whereby the two compounds may exert an additive or even synergistic effect on improving the condition.

The present invention also provides pharmaceutical compositions, for medical use, which include a pharmaceutically acceptable agent that blocks K—Cl cotransport in erythrocytes, an anti-hemoglobinopathic agent as described above, together with one or more pharmaceutically acceptable carriers thereof and optionally any other therapeutic ingredients.

The agents that block K—Cl cotransport are administered in effective amounts. In general, an effective amount is any amount that can cause inhibition of erythrocyte cell dehydration. Preferably an effective amount is that amount sufficient to cause a favorable phenotypic change in the condition such as a lessening, alleviation or elimination of a symptom or of a condition.

In general, an effective amount is that amount of a pharmaceutical preparation that alone, or together with further doses, produces the desired response. This may involve only slowing the progression of the disease temporarily, although more preferably, it involves halting the progression of the disease permanently or delaying the onset of or preventing the disease or condition from occurring. This can be monitored by routine methods. Generally, doses of active compounds would be from about 0.01 mg/kg per day to 1000 mg/kg per day. It is expected that doses ranging from 50–500 mg/kg will be suitable, preferably orally and in one or several administrations per day.

Such amounts will depend, of course, on the particular condition being treated, the severity of the condition, the individual patient parameters including age, physical condition, size and weight, the duration of the treatment, the nature of concurrent therapy (if any), the specific route of administration and other factors within the knowledge and expertise of the health practitioner. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agents that block K—Cl cotransport useful according to the invention may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. The term "pharmaceutically acceptable agents that block in a subject K—Cl cotransport" as used herein include only agents that block in a subject K—Cl cotransport that are non-toxic and which are suitable for administration into a human. Such "pharmaceutically acceptable" agents have very few, or preferably no serious side-effects, when administered in effective dosages to human subjects.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

In an important embodiment of this invention the pharmaceutical carrier may be a comestible product. A comestible as used herein is any type of edible food or drink containing at least one caloric compound and/or a cholesterol compound. For example, comestible products include dairy products such as milk and ice cream, baked goods such as cookies and cakes, gelled desserts, puddings, salad dressings, etc.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis, but very useful in treating acute episodes of the disease.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of agents that block K—Cl cotransport, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

Other delivery systems can include time-release, delayed release or sustained release delivery systems. Such systems can avoid repeated administrations of the active compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In another aspect of the invention, the pharmaceutically acceptable agent that blocks K—Cl cotransport in erythrocytes can be placed in a vial and be incorporated into a kit to be used in the treatment of a hemoglobinopathy such as sickle cell disease or thalassemia. In certain embodiments, anti-hemoglobinopathic agents according to the invention can also be placed in a vial and included in the same kit. The kits can include instructions or other printed material on how to administer the agents. In certain other embodiments the anti-hemoglobinopathic agent can be part of a kit that does not include agents that block K—Cl cotransport of the invention, but includes instructions or other printed material on how to combine the agent with a K—Cl cotransport inhibitor.

Figure 6:
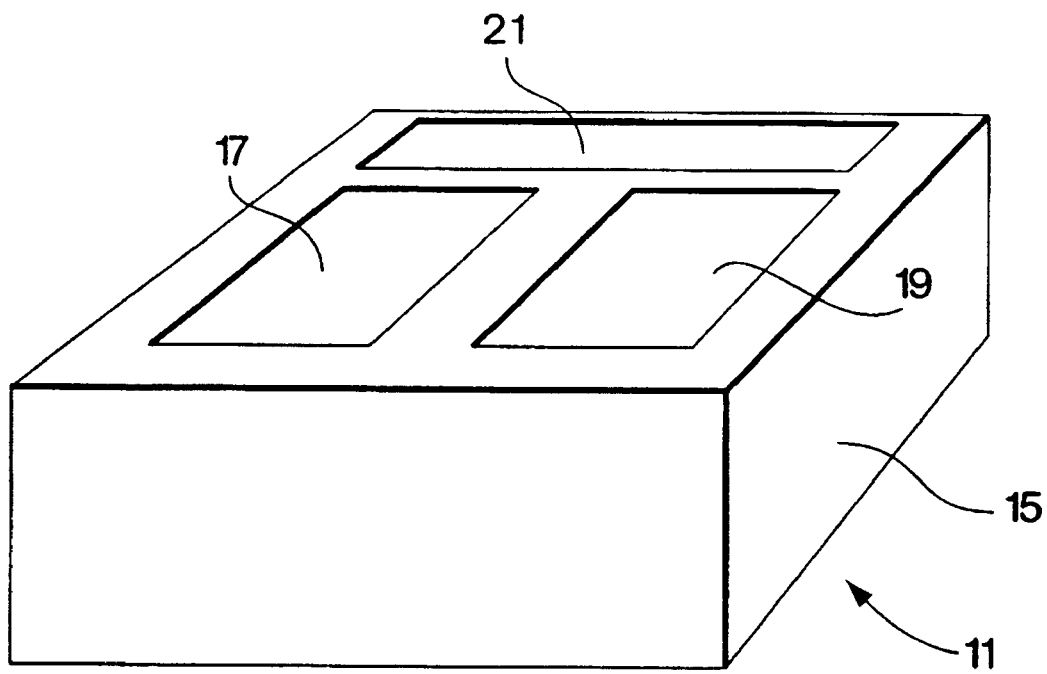

A kit embodying features of the present invention, generally designated by the numeral 11, is illustrated in FIG. 6. Kit 11 is comprised of the following major elements: packaging 15, a dosage form 17, a dosage form 19 and instructions 21. Packaging 15 is a box-like structure for holding dosage form 17, a dosage form 19 and instructions 21. Individuals skilled in the art can readily modify packaging 15 to suit individual needs.

Dosage form 17 comprises an agent that blocks K—Cl cotransport in an effective amount for administering to a subject. Dosage form 19 comprises an anti-hemoglobinopathic agent.

In the following examples, the unexpected beneficial in vivo effects of one K—Cl cotransport inhibitor of the invention (Mg pidolate) in the treatment of sickle cell disease, are established.

EXAMPLES

Experimental Procedures[1]

Patient Selection

Individuals over 18 years of age with SS disease were considered to be eligible for the study. Inclusion criteria included normal renal and liver function, performance status of 70% or greater, and no blood transfusions during the preceding 3 months. An investigator explained the study completely to each participant, who then gave written informed consent. A negative pregnancy test was required for female subjects. All the patients were treated as outpatients. No patients were hospitalized during the study.

[1] Abbreviations used herein: ALT, serum glutamic pyruvate transaminase; AST, serum glutamic oxaloacetic transaminase; BUN, blood urea nitrogen; CBC, complete blood count; CH, hemoglobin content; CV, corpuscular volume; D50, median density; DI, deformability index; DW, distribution width; Hb F, fetal hemoglobin; Hb S, sickle cell hemoglobin; HC, hemoglobin concentration; HDW, hemoglobin DW; M, mean; O, osmolality value in the hyperosmolar region at which the DI reaches half the maximum value; r, reticulocyte; R60, median 60% density range; RDW, red cell volume DW; SC, heterozygous for Hb S and C hemoglobin; SS, homozygous for Hb S; meq, milliequivalent.

Study Protocol

In the initial phase, erythrocyte and plasma Mg levels were determined in 21 patients with SS disease, 24 patients with SC disease, and 17 normal controls. 11 of the SS patients were enrolled in the dietary Mg supplementation study. One of the patients did not return after the baseline studies and could not be reached for follow-up. 10 patients completed the Mg supplementation protocol.

The following studies were performed three times (at the time of entry, after 2 weeks and after 4 weeks of Mg therapy): complete blood counts (CBC), electrolytes, blood urea nitrogen (BUN), creatinine, serum glutamic pyruvate transaminase (ALT), serum glutamic oxaloacetic transaminase (AST), total and direct bilirubin, erythrocyte phthalate density profiles, and membrane transport studies (described in detail below).

Subjects were given 0.6 meq Mg pidolate/kg body wt/day (MAG-2; Theraplix, Paris, France), divided into two oral daily doses, for 4 weeks. This dosage corresponds to 504 mg of supplemental Mg per day in a 70-kg subject. The daily Mg intake of normal subjects estimated from dietary history is 418±120 mg for males and 343±94 mg for females (Britton, J., et al., *Lancet*, 1994, 344: 357–362). This dosage is slightly higher in daily elemental Mg than the dose shown to increase erythrocyte Mg in two prior studies in patients with diabetes mellitus (Paolisso, G., et al., *J. Clin. Endocrinol. Metab.*, 1994, 78: 1510–1514; Borella, P., et al., *Magnes. Res.*, 1993, 6: 149–153). Mg pidolate was to be discontinued if the subjects experienced significant clinical or biochemical signs of Mg toxicity.

Hematological and Biochemical Studies

CBC, erythrocyte indices, and reticulocyte percentage were measured with a Technicon H*3 Hematology analyzer (Bayer Corp., Diagnostics Division, Tarrytown, N.Y.) (Mohandas, N., et al., *Blood*, 1986, 68: 506–513). After measuring directly the volume (V) and hemoglobin concentration (HC) of individual erythrocytes and reticulocytes, the instrument calculates the hemoglobin content (CH) of individual cells using the formula V×HC=CH. It also generates histograms and calculates distribution widths for each of these measured indices for reticulocytes: cell volume (MCV and RDW, MCVr and RDWr), cell hemoglobin concentration (CHCM and HDW, CHCMr and HDWr), and cell hemoglobin content (MCH and CHDW, CHr and CHDWr). MCHC is calculated from the measured hemoglobin and hematocrit values. We defined the number of dense SS erythrocytes as the absolute number of erythrocytes with CHCM>38 g/dl, from the direct cytometric measurement of CHCM. The Bayer H*3 analyzer identifies reticulocytes based on their absorbance after staining with the dye Oxazine 750. The amount of light absorbed by the reticulocytes is directly proportional to their RNA content (Brugnara, C., et al., *Am. J. Clin. Pathol.*, 1994, 102: 623–632).

We measured plasma levels of BUN, creatinine, ALT, AST, and other blood chemistries using standard assays on a chemistry analyzer (Boehringer/Hitachi 911; Hitachi Sci. Instr., Mountain View, Calif.).

Erythrocyte Composition, Density, and Ion Transport Studies

Erythrocyte cation content and erythrocyte density distribution curves, using phthalate esters, were determined as described previously (Danon, D., and Marikovsky, Y., *J. Lab. Clin. Med.* 1964, 64: 668–674).

We evaluated three parameters in the phthalate esters assay (Rodgers, G P, et al., *J. Lab. Clin. Med.*, 1985, 106: 30–37): (a) D50, or median density, the density value that divides the red cell population in half; (b) R60, or median 60% density range obtained after subtracting the 20% lightest and densest fractions, quantifies the spread in cell densities which is characteristic of SS disease; and (c) percentage of dense cells, corresponding to the percentage of cells with density>1.120. With these values and the absolute erythrocyte count obtained from the CBC, the absolute number of so-defined dense cells per microliter can be calculated. Repeated measurements in different patients indicate that the reproducibility of these assays (expressed as mean±SD of the individual cell volume for eight patients) is 0.11±0.07% for D50 and 12.7±7.3% for the percentage of dense cells. Plasma and buffy coat were removed after centrifugation at 1,200 g for 10 min, and the cells were washed four times with choline wash solution containing 152 mmol/liter choline chloride, 1 mmol/liter Tris-Mops, pH 7.4, at 4° C. Erythrocyte K and Na contents were determined with atomic absorption spectrometry. Repeated measurements in different patients indicate that the reproducibility of the erythrocyte K content assay (expressed as mean±SD of the individual cell volume for eight patients) is 4.6±2.7%. K—Cl cotransport from fresh cells was measured as chloride-dependent net K efflux into hypotonic medium. Flux medium for chloride-dependent K efflux contained (in mmol/liter) 100 Na, 1 Mg (the anion either Cl or $NO_3$), 10 glucose and 10 Tris-Mops (pH 7.4 at 37° C.).

Chloride-dependent K efflux was calculated from the difference between K efflux into chloride and that into nitrate. Efflux rates were calculated from net flux measurements taken after 5 and 25 min of incubation at 37° C. Repeated measurements in different patients indicate that the reproducibility of these assays (expressed as mean+SD of the individual CV for eight patients) is 10.9±5%. The maximal rates of Na—K pump and Na—K—2Cl cotransport systems were measured in cells containing equal amounts of Na and K (~50 mmol/liter of cells each). Erythrocytes were treated with the nystatin technique to modify the intracellular cation composition (Brugnara, C., et al., *J. Clin. Invest.*, 1985, 75: 1608–1617). The nystatin-loading solution contained (in mmol/liter) 70 NaCl, 70 KCl, and 55 sucrose. Na—K pump was estimated as the ouabain-sensitive fraction on Na efflux into a medium containing (in mmol/liter) 130 choline chloride and 10 KCl. Triplicate samples were incubated for 5 min and 25 min at 37° C. The ouabain concentration was 0.1 mmol/liter. Na—K—2Cl cotransport was estimated as the bumetanide-sensitive fraction of Na efflux into a medium containing (in mmol/liter)

140 choline chloride and 0.1 ouabain. The efflux times were 5 and 25 min at 37° C. with triplicate samples. The bumetanide concentration was 0.01 mmol/liter. All media contained (in mmol/liter) 1 $MgCl_2$, 10 glucose, and 10 Tris-Mops (pH 7.4 at 37° C.).

Osmotic Gradient Ektacytometry

Osmotic gradient ektacytometry was used to quantitate cellular deformability, which is regulated by surface area, surface area-to-volume ratio, and state of hydration of red cells (Clark, M R, et al, *Blood*, 1983, 61: 899–910). Osmotic gradient ektacytometry was performed on fresh blood samples in five of the patients enrolled in the trial, at baseline and after 4 weeks of Mg supplementation. Two of these patients were also studied after 2 weeks of therapy. Erythrocytes were continuously mixed with a 4% polyvinylpyrrolidone solution of gradually increasing osmolality (from 60 to 450 mosM), and the deformability index was recorded with an ektacytometer (Bayer Corp., Diagnostics Division) as a function of osmolality at a constant applied shear stress of 170 dynes/cm2. The following variables were quantified:

(a) Omin, the osmolality at which the deformability index (DI) reaches a minimum in the hypotonic region of the gradient, corresponds to the osmolality at which 50% of the red cells hemolyze in a standard osmotic fragility test. This index provides a measure of the average surface area-to-volume ratio of the erythrocytes.

(b) DImax, the maximum value of the DI attained at physiologically relevant osmolality, is quantitatively related to the mean surface area of red cells.

(c) O, the osmolality value in the hyperosmolar region at which the DI reaches half the maximum value, provides information on the hydration state of the erythrocytes.

Osmotic gradient ektacytometry quantitates the surface area-to-volume ratio, the membrane surface area, and the state of hydration of erythrocytes in the blood sample. Normal ranges for these different parameters had been established in our laboratory with. blood samples from 144 healthy adult blood donors (Cynober, T., et al., *J. Lab. Clin. Med.*, 1996, 128:259–269).

Erythrocytes of patients with SS disease show, to a variable extent, a left shift in Omin, a left shift in O, indicative of red cell dehydration, and a decrease in DImax, which most likely reflects heterogeneity in cell water content rather than a uniform reduction in surface area.

Statistical Analysis

All values are means±SD. Comparisons of separate variables between baseline state and values after 14 and 28 days of treatment were performed using two-tailed Student's t-test. Comparison of more than two groups was performed by one-way ANOVA with Tukey's test for post hoc comparison of the means (Godfrey, K., *N. Engl. J. Med.*, 1985, 313: 1450–1456).

Example 1

Serum and Erythrocyte Mg in SS and SC Disease

FIG. 1 presents data on the erythrocyte Mg content of patients with SS or SC disease and normal control subjects. The SS and SC erythrocytes have a reduced erythrocyte Mg content compared with normal controls (in mmol/kg hemoglobin, 6.6±1.2, n=21, 6.2±0.9, n=24, and 8.62±0.8, n =17, P<0.05, respectively). Levels of plasma Mg were no different in SS and SC patients than in normal controls (data not shown).

Example 2

The Effect of Dietary Mg Supplementation on SS Erythrocyte Mg. Na. and K Contents Table I presents data obtained from measurements of plasma and erythrocyte Mg in the 10 SS disease patients treated with Mg pidolate. Dietary Mg supplementation did not affect plasma Mg, which remained unchanged from baseline. A significant increase in erythrocyte Mg content was observed after 14 and 28 days of Mg supplementation, with values similar to those of normal cells at day 14, but somewhat higher than normal cells at day 28. These changes are much greater than those obtained with slightly lower doses of Mg pidolate in subjects with diabetes mellitus, who had normal baseline erythrocyte Mg content (Paolisso, G., et al., *J. Clin. Endocrinol Metab.*, 1994, 78: 1510–1514; Borella, P., et al., *Magnes. Res.*, 1993, 6:149–153).

TABLE I

Plasma and Erythrocyte Mg at Baseline and during Dietary Mg Supplementation

| Time d | Plasma Mg mM | Erythrocyte Mg mmol/kg Hb |
|---|---|---|
| Baseline | 0.862 ± 0.057 (11) | 5.18 ± 0.24 (11) |
| 14 | 0.954 ± 0.11 (10) | 9.34 ± 2.3 (10)* |
| 28 | 0.937 ± 0.09 (10) | 11.4 ± 1.2‡ |

Patients were treated with oral Mg pidolate at 0.6 meq/kg body wt/d. Data are presented as means ± SD (n of determinations). *P < 0.05 and ‡P < 0.005 compared to baseline.

Figure 2:
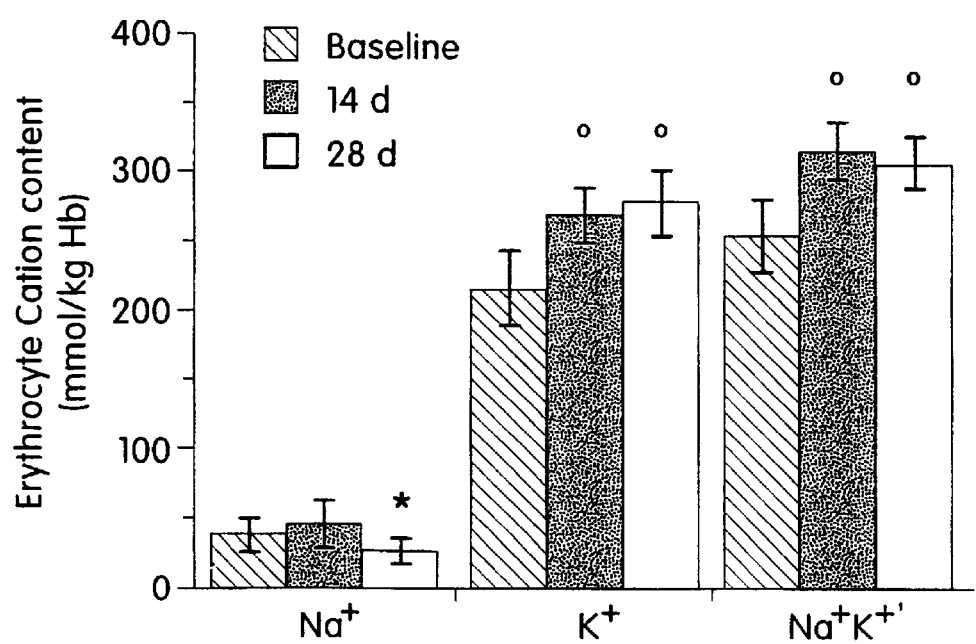
FIG. 2 depicts erythrocyte cation content in patients with SS disease at baseline and after 14 and 28 d of oral Mg pidolate supplements.

FIG. 2 presents the data obtained from measurements of erythrocyte Na and K content. As shown in previous publications (Clark, M R, et al., *J. Clin. Invest.*, 1978, 62: 329–337; Brugnara, C., et al., *Science*, 1986, 232: 388–390), baseline erythrocyte K was markedly lower, and erythrocyte Na was higher in SS and SC erythrocytes compared with normal controls. Statistically significant increases in SS erythrocyte K and total cation content with pidolate administration were noted at day 14 and persisted at day 28. There was also a statistically significant decrease in cell Na content at day 28.

Example 3

Figure 3A:
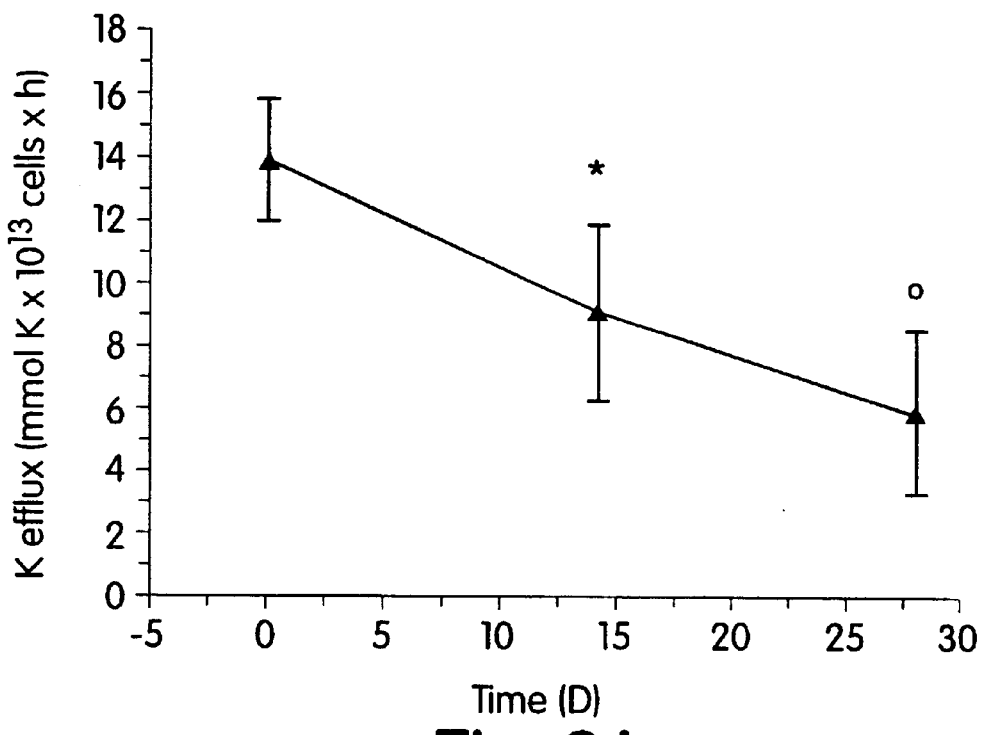
FIG. 3 shows the activity of erythrocyte K—Cl cotransport (A), Na—K pump and Na—K—Cl cotransport (B), at baseline and after 14 and 28 d of oral Mg pidolate supplements in patients with SS disease.
Figure 3B:
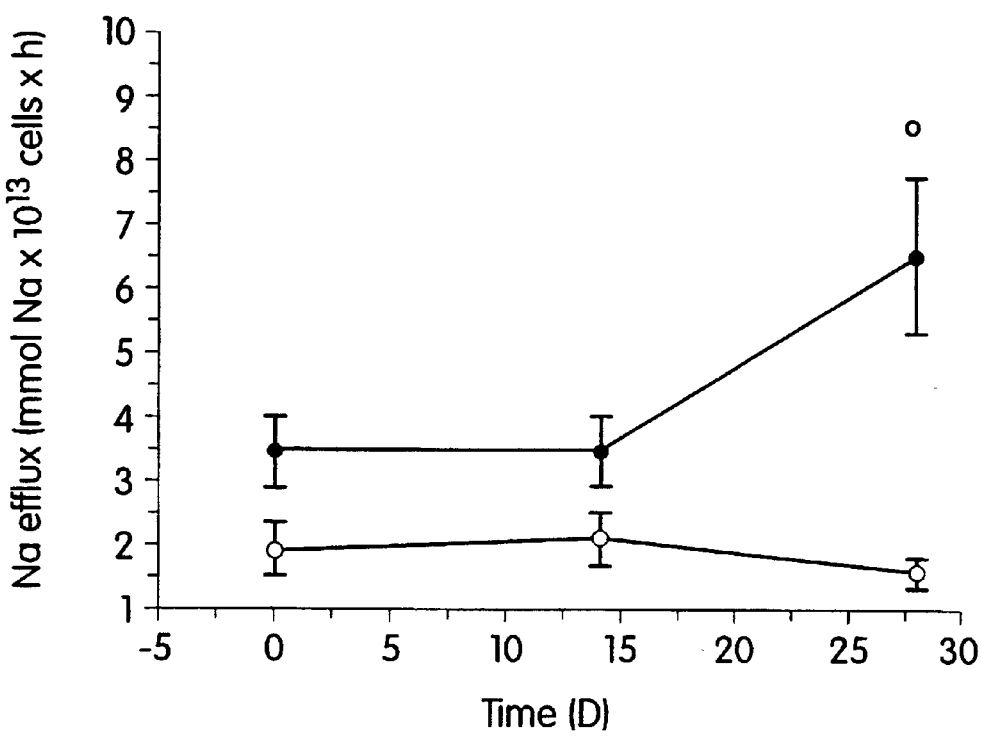

The Effect of Dietary Mg Supplementation on the Major Ion Transport Pathways of SS Erythrocytes FIG. 3 presents data obtained from measurements of erythrocyte K—Cl cotransport, Na—K pump, and Na—K—Cl cotransport activities. A significant reduction in K—Cl cotransport activity was observed at day 14, with a further decrease at day 28. This finding is most likely related to the increased cell Mg content, and provides a mechanistic explanation for the observed increase in cell K content.

Significant changes were also observed in the maximal rate of the Na—K pump. The baseline level of Na—K pump activity is abnormally low in SS erythrocytes, as has been previously reported by other investigators (Clark, M R, et al., *J. Clin. Invest.*, 1978, 62: 329–337; Ortiz, O E, et al., *J. Physiol.*, 1990, 427: 211–226). 28 days of dietary Mg supplementation induced a significant increase in the maximal rate of this transporter, which reached values similar to those observed in normal controls. This finding suggests that either the total number of pumps per erythrocyte or the catalytic rate of the pump had been increased as a consequence of the increased erythrocyte Mg content.

No significant changes were observed in the maximal rate of the Na—K—Cl cotransport, the other major cotransporter of erythrocytes.

Example 4

Figure 4:
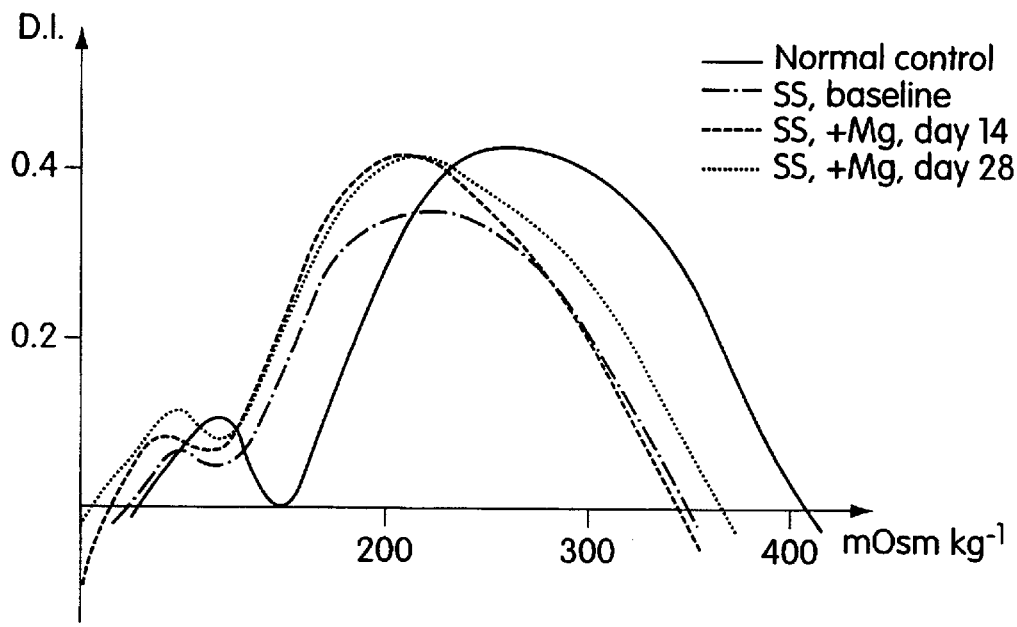
FIG. 4 shows a diagram for the osmotic deformability profile for erythrocytes collected from a patient with SS disease at baseline and after 14 and 28 d of oral Mg pidolate supplementation.

The Effect of Dietary Mg Supplementation on the Cellular Deformability of SS Erythrocytes FIG. 4 and Table II present data obtained from osmotic gradient ektacytometry determinations. Studies were carried out at baseline and after 28 days of Mg supplementation in five patients. FIG. 4 shows that in one representative patient, a significant change in the erythrocyte deformability index occurred with dietary Mg supplementation, in the direction of the values observed in normal controls. A statistically significant increase in O values indicated an improved hydration state of the erythrocytes (Table II).

Plasma Mg, BUN, and creatinine did not change during Mg supplementation (Table I).

Conclusion

Additionally, erythrocyte Mg content of SS and SC patients was reduced compared with normal controls (FIG. 1) A large study also reported lower levels of erythrocyte Mg

TABLE II

Hematological Parameters in Sickle Cell Patients at Baseline and during Mg Supplementation

| Time d | Hb g/dl | MCV fl | MCHC g/dl | Retic. $10^3/\mu l$ | H Retic. $10^3/\mu l$ | $D_{50}$ | $D_{60}$ | 0' mos M kg |
|---|---|---|---|---|---|---|---|---|
| Baseline | 8.1 ± 1.0 | 90.2 ± 9.0 | 33.2 ± 1.4 | 285 ± 72 | 30.2 ± 10.2 | 1.098 ± 0.002 | 0.013 ± 0.003 | 296.4 ± 20.1 |
| 14 | 8.2 ± 1.0 | 89.5 ± 8.9 | 33.5 ± 1.5 | 269 ± 73.5 | 30.6 ± 18.8 | 1.091 ± 0.005‡ | 0.010 ± 0.004* | ND |
| 28 | 8.5 ± 1.1 | 90.0 ± 9.0 | 32.4 ± 0.8 | 228 ± 34.3* | 23.9 ± 6.8* | 1.092 ± 0.004‡ | 0.010 ± 0.001* | 306.4 ± 15.3* |

Patients were treated with oral Mg pidolate at 0.6 meq/kg/d. Data are presented as mean ± SD (n = 10). *P, 0.05 and *P, 0.005 compared to baseline. Retic., reticulocytes. Hretic., high staining intensity reticulocytes. ND not determined.

Table II presents results obtained from the determination of several hematological and biochemical parameters. A trend for an increase in hemoglobin levels did not reach statistical significance. No significant changes occurred in MCV, MCHC, and MCH, nor in the distribution widths RDW and HDW and values for MCH.

A significant reduction occurred in the absolute reticulocyte count after 28 days (Table II). This reduction was associated with a significant reduction in the absolute number of reticulocytes with high staining intensity, which corresponds to the most immature fraction of reticulocytes, and which has the highest residual RNA content. No significant changes occurred in the absolute number of reticulocytes with low and medium staining intensity. Other cellular characteristics of the reticulocytes were unchanged, such as reticulocyte cell volume (MCVr: 113±7.6, 107±4.4, and 108.8±5.3, at baseline, 14, and 28 d, respectively) and reticulocyte cell hemoglobin concentration (CHCMr: 26.3±2.1, 27.4±1.5, and 27±1.0 at baseline, 14, and 28 days, respectively).

Table II additionally shows significant changes in the density of the SS erythrocytes with Mg therapy. The median density of erythrocytes fell significantly after 14 and 28 days of dietary Mg supplementation (Table II). The middle density range (R60), which quantifies the heterogeneous distribution of erythrocyte densities, was also reduced significantly with dietary Mg supplementation.

Figure 5:
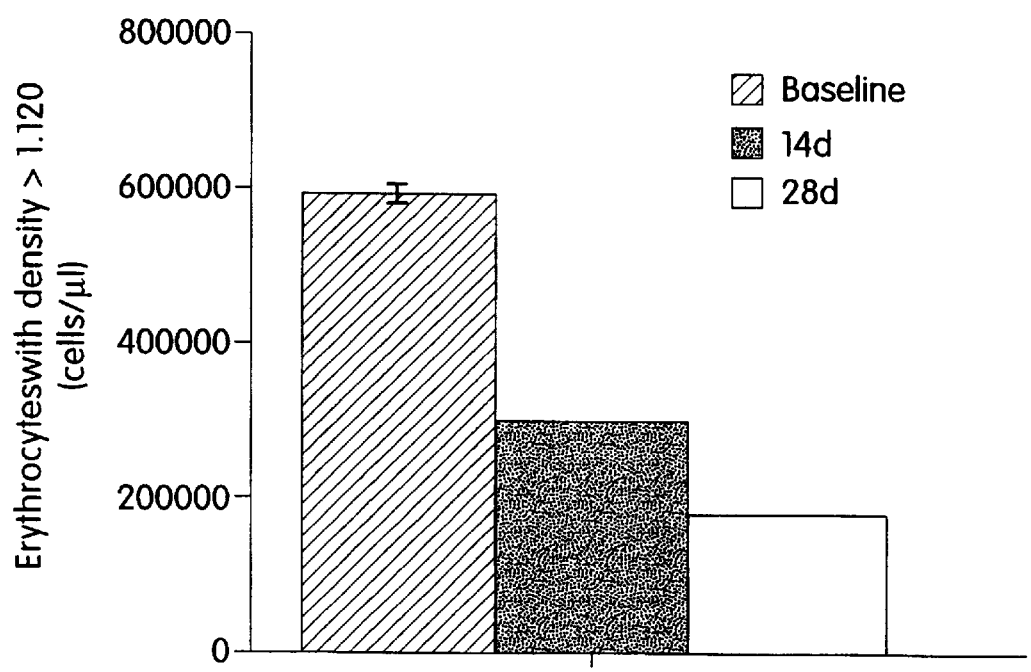
FIG. 5 depicts the absolute number of dense erythrocytes at baseline, and after 14 and 28 d of oral Mg supplements in patients with SS disease.

FIG. 5 shows that a significant reduction in the absolute number of dense, dehydrated SS erythrocytes, was observed after 14 and 28 days of Mg supplementation. These data were obtained with the phthalate density profile method, which quantifies cells with density>1.120. Estimates of dense cells based on the Bayer H*3 analyzer, which quantifies erythrocytes with a CHCM value>38 g/dl, also showed a significant reduction of dense cells after 28 d of Mg therapy.

Example 5

Clinical and Side Effects of Dietary Mg Supplementation

No significant side effects of dietary Mg supplementation were noted in this trial, with the exception of transient diarrhea in 1 of the 10 patients. No significant changes were observed in plasma levels of ALT, AST, or indirect bilirubin.

in SS disease (Olukoga, A O, et al., *East Afr. Med. J.*, 1990, 67: 348–354). Most of the Mg contained in erythrocytes is bound to cellular proteins, ATP, and 2,3-diphosphoglycerate. The normal erythrocyte membrane is functionally impermeable to Mg. The Na/Mg exchanger, which extrudes Mg from the cell in exchange for Na, provides the only known mechanism for Mg loss in normal erythrocytes (Feray, J C. and Garay, R., *Became. Beefiest. Acta*, 1986, 856: 76–84), but remains poorly understood. This system most likely mediates the decrease in erythrocyte Mg observed with cell age (or density): a two to fourfold difference in cell Mg has been described between high and low density fractions of human erythrocytes (Bernstein, R E, *J. Clin. Invest.* 1959, 38: 1572–1586; Ginsberg, S., et al., *Blood*, 1962, 20: 722–729). A preliminary report of increased activity of the Na/Mg exchanger in Mg-loaded SS erythrocytes (Feray, J C, et al., *VI International Magnesium Symposium*, 1988, Abstract 22a) might provide an explanation for the reduced Mg content of SS cells. The reduction in total cell Mg content is evident particularly in dense SS erythrocytes. In addition, these cells exhibit an abnormal increase in free Mg due to reduction in the intracellular Mg buffering capacity (Ortiz, O E, et al., *J. Physiol.*, 1990, 427: 211–226). This may promote further Mg loss upon sickling, because the free Mg gradient is outwardly directed, and sickling has been shown to increase the permeability of the erythrocyte membrane to Mg (Ortiz, O E, et al., *J. Physiol.*, 1990, 427: 211–226). The data described herein indicate that the reduced erythrocyte Mg of SS erythrocytes can be restored to normal or above normal values in patients treated with dietary Mg supplements (Table I).

The normalization of erythrocyte Mg content is associated with a significant reduction in K—Cl cotransport activity and with increased K content. The reduced K—Cl cotransport can be interpreted as a direct effect of increased Mg content, although indirect effects are possible, including reduction in absolute reticulocyte number or diminished oxidative damage. K—Cl cotransport is the primary mechanism for dehydration of transferrin receptor-positive reticulocytes (Franco, R S, et al., *J. Clin. Invest.*, 1995, 95: 2573–2580).

Mg is an important regulator of ion transport across cellular membranes. Mg is an essential cofactor for Na-stimulated phosphorylation of the Na—K atpase (Flagman, P and Lew, V., *J. Physiol.*, 1981, 315: 421446). A [Mg]/[ATP] ratio near one is optimal for Na—K pump activity, with inhibition at higher and lower ratios. It has been demonstrated that the reduced Na—K pump activity of dense SS erythrocytes can be normalized when a proper [Mg]/[ATP] ratio is restored (Ortiz, O E, et al., *J. Physiol.*, 1990, 427: 211–226). The observed changes in the maximal rate of the Na—K pump (FIG. 3) indicate that the optimal [Mg]/[ATP] ratio has been restored with dietary Mg supplements.

A finding shared by this clinical trial and our recently published report on the use of clotrimazole in SS disease (Brugnara, C.,et al.,*J. Clin. Invest.*, 1996, 97: 1227–1234) is the observation of a reduction in the number of circulating dense SS erythrocytes. These two studies together indicate that both the Gardos channel and the K—Cl cotransporter are involved in the in vivo generation of dense SS cells.

The reduction in both absolute reticulocyte counts and percentage of immature reticulocytes induced by Mg therapy suggests an improvement of the anemia. The improved erythrocyte deformability observed in this study suggests that survival and/or oxygen delivery are enhanced.

This study provides the first in vivo evidence for a role of K—Cl cotransport in SS erythrocyte dehydration.

DETAILED DESCRIPTION OF THE DRAWINGS

FIG. 1. Erythrocyte Mg content (mean±SD) in normal controls (AA, n=17) and in untransfused patients with SS (n=21) and SC (n=24) disease.

FIG. 2. Erythrocyte cation content in patients with SS disease at baseline and after 14 and 28 d of oral Mg pidolate supplements (0.6 meq/kg body wt/d, n=10). *P<0.05 and °P<0.005.

FIG. 3. Activity of erythrocyte K—Cl cotransport (▲) (A), Na—K pump (●) and Na—K—Cl cotransport (○) (B), at baseline and after 14 and 28 d of oral Mg pidolate supplements (0.6 meq/kg body wt/d, n=10) in patients with SS disease. *P<0.05 and °P<0.005.

FIG. 4. Osmotic deformability profile for erythrocytes collected from a patient with SS disease at baseline and after 14 and 28 d of oral Mg pidolate supplementation (0.6 meq/kg body wt/d). A profile of normal control cells is also presented. A significant shift in O' indicates an improved hydration state of the SS erythrocytes after Mg supplementation.

FIG. 5. Absolute number of dense erythrocytes (cells/μl) at baseline, and after 14 and 28 d of oral Mg supplements in patients with SS disease. Data obtained with phthalate density profiles. Dense cells were defined as the percentage of cells with density>1.120. Absolute number of dense erythrocytes was obtained from the percentage of dense cells and the erythrocyte count obtained with the Bayer H*3 analyzer.

All references disclosed herein are incorporated by reference in their entirety.

We claim:

1. A pharmaceutical composition, comprising:
   a pharmaceutically acceptable agent that blocks K—Cl cotransport in an erythrocyte of a subject,
   an anti-hemoglobinopathic agent other than said agent that blocks K—Cl cotransport in an erythrocyte of a subject, and
   a pharmaceutically acceptable carrier.

2. A kit comprising:
   a package housing a container containing a pharmaceutically acceptable agent that blocks in a subject K—Cl cotransport in erythrocytes of the subject, in an amount effective to inhibit erythrocyte cell dehydration, and housing instructions for using said agent to treat erythrocyte cell dehydration, in a subject in need of such treatment.

3. A method for inhibiting erythrocyte cell dehydration in a subject, comprising: administering to a subject in need of such treatment a pharmaceutically acceptable agent that blocks in a subject K—Cl cotransport in erythrocytes of the subject, in an amount effective to inhibit erythrocyte cell dehydration in the subject.

4. The method of claim 3, wherein the pharmaceutically acceptable agent is of the general formula:

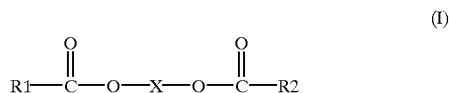

(I)

wherein X is a divalent cation, and
wherein R1 and R2 each is an aryl group or a heteroaryl group which can be unsubstituted, or substituted with substituents selected from the group consisting of $(C_1-C_6)$ alkyl, $(C_1-C_6)$ alkenyl and $(C_1-C_6)$ alkynyl, —CN, —OR', —SR', —NO$_2$, —NR'R', halogen, amino acid, —R", —C(O)R", —C(S)R", —C(O)OR", —C(S)OR", —C(O)SR", —C(S)SR", —C(O)N(R")$_2$, —C(O)C(O)R", —C(S)C(O)R", —C(O)C(S)R", —C(S)C(S)R", —C(O)C(O)OR", —C(S)C(O)OR", —C(O)C(S)OR", —C(O)C(O)SR", —C(S)C(S)OR", —C(S)C(O)SR", —C(O)C(S)SR", —C(S)C(S)SR", —C(O)C(O)N(R")$_2$, —C(S)C(O)N(R")$_2$, —C(O)C(S)N(R")$_2$, or —C(S)C(S)N(R")$_2$,
wherein each R' is independently selected from the group consisting of —H, $(C_1-C_6)$ alkyl, $(C_1-C_6)$ alkenyl and $(C_1-C_6)$ alkynyl, and
wherein each R" is independently selected from the group consisting of —H, $(C_1-C_6)$ alkyl, $(C_1-C_6)$ alkenyl, $(C_1-C_6)$ alkynyl, $(C_6-C_{20})$ aryl, $(C_6-C_{20})$ substituted aryl, $(C_6-C_{26})$alkaryl and substituted $(C_6-C_{26})$ alkaryl, and the aryl and alkaryl substituents are each independently selected from the group consisting of —CN, —OR', —SR', —NO$_2$, —NR'R', halogen, $(C_1-C_6)$ alkyl, $(C_1-C_6)$ alkenyl, $(C_1-C_6)$ alkynyl and trihalomethyl.

5. The method of claim 4, wherein at least one of R1 and R2 is 2-pyrrolidone.

6. The method of claim 5, wherein the agent is:

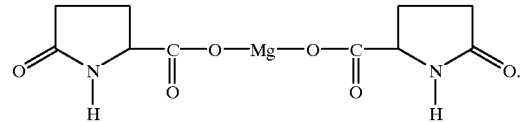

7. The method of claim 4–6, wherein said divalent cation X is selected from the group consisting of Mg, Ca, Mn, Sr and Zn.

8. The method of claim 7, wherein said divalent cation X is Mg.

9. The method of claim 3–6, wherein said subject suffers from sickle cell disease.

10. The method of claim 3–6, wherein said subject suffers from thalassemia.

11. The method of claim 3–6, wherein said administration is per oral.

12. The method of claim 3–6, wherein said administration is parenteral.

13. The method of claim 3–6, wherein said administration is intravenous.

14. The method of claim 3–6, further comprising administering an anti-hemoglobinopathic agent, other than said agent that blocks K—Cl cotransport in an erydhrocyte of a subject.

15. A method for inhibiting erythrocyte cell dehydration, comprising:

contacting an erythrocyte cell with an agent that blocks K—Cl cotransport in an erythrocyte, in an amount effective to inhibit erythrocyte cell dehydration, wherein the agent is of the general formula:

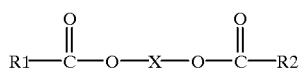

(I)

wherein X is a divalent cation, and wherein R1 and R2 each is an aryl group or a heteroaryl group which can be unsubstituted, or substituted with substituents selected from the group consisting of $(C_1-C_6)$ alkyl, $(C_1-C_6)$ alkenyl and $(C_1-C_6)$ alkynyl, —CN, —OR', —SR', —NO$_2$, —NR'R', halogen, amino acid, —R", —C(O)R", —C(S)R", —C(O)OR", —C(S)OR", —C(O)SR", —C(S)SR", —C(O)N(R")$_2$, —C(O)C(O)R", —C(S)C(O)R", —C(O)C(S)R", —C(S)C(S)R", —C(O)C(O)OR", —C(S)C(O)OR", —C(O)C(S)OR", —C(O)C(O)SR", —C(S)C(S)OR", —C(S)C(O)SR", —C(O)C(S)SR", —C(S)C(S)SR", —C(O)C(O)N(R")$_2$, —C(S)C(O)N(R')$_2$, —C(O)C(S)N(R")$_2$, or —C(S)C(S)N(R")$_2$, wherein each R' is independently selected from the group consisting of —H, $(C_1-C_6)$ alkyl, $(C_1-C_6)$ alkenyl and $(C_1-C_6)$ alkynyl, and wherein each R" is independently selected from the group consisting of —H, $(C_1-C_6)$ alkyl, $(C_1-C_6)$ alkenyl, $(C_1-C_6)$ alkynyl, $(C_6-C_{20})$ aryl, $(C_6-C_{20})$ substituted aryl, $(C_6-C_{26})$ alkaryl and substituted $(C_6-C_{26})$ alkaryl, and the aryl and alkaryl substituents are each independently selected from the group consisting of —CN, —OR', —SR', —NO$_2$, —NR'R', halogen, $(C_1-C_6)$ alkyl, $(C_1-C_6)$ alkenyl, $(C_1-C_6)$ alkynyl and trihalomethyl.

16. The method of claim 14, wherein said anti-hemoglobinopathic agent inhibits erythrocyte cell dehydration.

17. The method of claim 14, wherein said anti-hemoglobinopathic agent inhibits sickle hemoglobin polymerization.

18. The method of claim 14, wherein said anti-hemoglobinopathic agent increases fetal hemoglobin production.

19. The method of claim 14, wherein said anti-hemoglobinopathic agent increases microvascular blood flow.

20. The method of claim 7, further comprising administering an anti-hemoglobinopathic agent, other than said agent that blocks K–Cl cotransport in an erythrocyte of a subject.

21. The method of claim 20, wherein said anti-hemoglobinopathic agent inhibits erythrocyte cell dehydration.

22. The method of claim 20, wherein said anti-hemoglobinopathic agent inhibits sickle hemoglobin polymerization.

23. The method of claim 20, wherein said anti-hemoglobinopathic agent increases fetal hemoglobin production.

24. The method of claim 20, wherein said anti-hemoglobinopathic agent increases microvascular blood flow.

25. The method of claim 8, further comprising administering an anti-hemoglobinopathic agent, other than said agent that blocks K–Cl cotransport in an erythrocyte of a subject.

26. The method of claim 8, wherein said anti-hemoglobinopathic agent inhibits erythrocyte cell dehydration.

27. The method of claim 8, wherein said anti-hemoglobinopathic agent inhibits sickle hemoglobin polymerization.

28. The method of claim 8, wherein said anti-hemoglobinopathic agent increases fetal hemoglobin production.

29. The method of claim 8, wherein said anti-hemoglobinopathic agent increases microvascular blood flow.

30. The method of claim 15, wherein at least one of R1 and R2 is 2-pyrrolidone.

31. The method of claim 30, wherein the agent is:

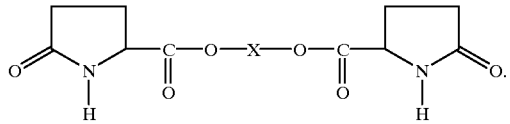

32. The method of claim 15, wherein said divalent cation X is selected from the group consisting of Mg, Ca, Mn, Sr and Zn.

33. The method of claim 32, wherein said divalent cation X is Mg.

34. The method of claim 15, further comprising contacting the erythrocyte cell with an anti-hemoglobinopathic agent, other than said agent that block K–Cl contransport in an erythrocyte.

35. The pharmaceutical composition of claim 1, wherein the pharmaceutically acceptable agent that blocks K–Cl contransport in an erythrocyte is of the general formula:

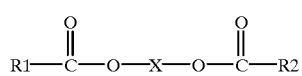

(I)

wherein X is a divalent cation, and wherein R1 and R2 each is an aryl group or a heteroaryl group which can be unsubstituted, or substituted with substituents selected from the group consisting of $(C_1-C_6)$ alkyl, $(C_1-C_6)$ alkenyl and $(C_1-C_6)$ alkynyl, —CN, —OR', —SR', —NO$_2$, —NR'R', halogen, amino acid, —R", —C(O)R", —C(S)R", —C(O)OR", —C(S)OR", —C(O)SR", —C(S)SR", —C(O)N(R")$_2$, —C(O)C(O)R", —C(S)C(O)R", —C(O)C(S)R", —C(S)C(S)R", —C(O)C(O)OR", —C(S)C(O)OR", —C(O)C(S)OR", —C(O)C(O)SR", —C(S)C(S)OR", —C(S)C(O)SR", —C(O)C(S)SR", —C(S)C(S)SR", —C(O)C(O)N(R")$_2$, —C(S)C(O)N(R")$_2$, —C(O)C(S)N(R")$_2$, or —C(S)C(S)N(R")$_2$, wherein each R' is independently selected from the group consisting of —H, $(C_1-C_6)$ alkyl,$(C_1-C_6)$ alkenyl and $(C_1-C_6)$ alkynyl, and wherein each R" is independently selected from the group consisting of —H, $(C_1-C_6)$ alkyl, $(C_1-C_6)$ alkenyl, $(C_1-C_6)$ alkynyl, $(C_6-C_{20})$ aryl, $(C_6-C_{20})$ substituted aryl, $(C_6-C_{26})$ alkaryl and substituted $(C_6-C_{26})$ alkaryl, and the aryl and alkaryl substituents are each independently selected from the group consisting of —CN, —OR', —SR', —NO$_2$, —NR'R', halogen, $(C_1-C_6)$ alkyl, $(C_1-C_6)$ alkenyl, $(C_1-C_6)$ alkynyl and trihalomethyl.

36. The pharmaceutical composotion of claim 35, wherein at least one of R1 and R2 is 2-pyrrolidone.

37. The pharmaceutical composition of claim 36, wherein the agent is:

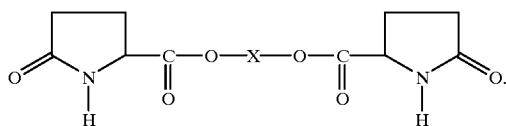

38. The pharmaceutical composition of claim 35, wherein said divalent cation X is selected from the group consisiting of Mg, Ca, Mn, Sr and Zn.

39. The pharmaceutical composition of claim 38, wherein said divalent cation X is Mg.

40. The pharmaceutical composition of claim 1, wherein said pharmaceutically acceptable carrier is a comestible product.

41. The pharmaceutical composition of claim 35, wherein said pharmaceutically acceptable carrier is a comestible product.

42. The pharmaceutical composition of claim 39, wherein said pharmaceutically acceptable carrier is a comestible product.

43. The pharmaceutical composition of claim 1, wherein said anti-hemoglobinopathic agent is selected from the group consisting of an erythrocyte cell dehydration inhibitor, a sickle hemoglobin inhibitor, an agent that increases fetal hemoglobin production and an agent that increases microvascular blood flow.

44. The pharmaceutical composition of claims 39, wherein said antihemoglobinopathic agent is selecfted from the group consisting of an erythrocyte cell dehydration inhibitor, a sickle hemoglobin inhibitor, an agent that increases fetal hemoglobin production and an agent that increases microvascular blood flow.

45. The kit of claim 2, wherein said agent is of the general formula:

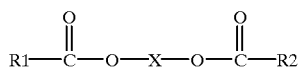 (I)

wherein X is a divalent cation, and wherein R1 and R2 each is an aryl group or a heteroaryl group which can be unsubstituted, or substituted with substituents selected from the group consisting of $(C_1-C_6)$ alkyl, $(C_1-C_6)$ alkenyl and $(C_1-C_6)$ alkynyl, —CN, —OR', —SR', —NO$_2$, —NR'R', halogen, amino acid, -R", —C(O)R", —C(S)R", —C(O)OR", —C(S)OR", —C(O)SR", —C(S)SR", —C(O)N(R")$_2$, —C(O)C(O)R", —C(S)C(O)R", —C(O)C(S)R", —C(S)C(S)R", —C(O)C(O)OR", —C(S)C(O)OR", —C(O)C(S)OR", —C(O)C(O)SR", —C(S)C(S)OR", —C(S)C(O)SR", —C(O)C(S)SR", —C(S)C(S)SR", —C(O)C(O)N(R")$_2$, —C(S)C(O)N(R")$_2$, —C(O)C(S)N(R")$_2$, or —C(S)C(S)N(R")$_2$, wherein each R'is independently selected from the group consisting of —H, $(C_1-C_6)$ alkyl, $(C_1-C_6)$ alkenyl and $(C_1-C_6)$ alkynyl, and wherein each R" is independently selected from the group consisting of —H, $(C_1-C_6)$ alkyl, $(C_1-C_6)$ alkenyl, $(C_1-C_6)$ alkynyl, $(C_6-C_{20})$ aryl, $(C_6-C_{20})$ substituted aryl, $(C_6-C_{26})$ alkaryl and substituted $(C_6-C_{26})$ alkaryl, and the aryl and alkaryl substituents are each independently selected from the group consisting of —CN, —OR', —SR', —NO$_2$, —NR'R', halogen, $(C_1-C_6)$ alkyl, $(C_1-C_6)$ alkyl, $(C_1-C_6)$ alkynyl and trihalomethyl.

46. The kit of claim 45, wherein at least one of R1 and R2 is 2-pyrrolidone.

47. The kit of claim 46, wherein the agent is:

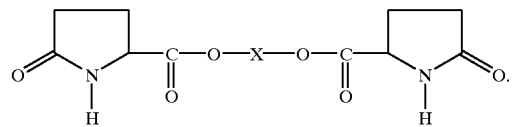

48. The kit of claim 45, wherein said divalent cation X is selected from the group consisting of Mg, Ca, Mn, Sr, and Zn.

49. The kit of claim 48, wherein said divalent cation X is Mg.

50. The kit of claim 2, further comprising, a container containing an anti-hemoglobinopathic agent other than said agent that blocks K-Cl cotransport in erythrocytes of the subject.

51. The kit of claim 45, further comprising, a container containing an anti-hemoglobinopathic agent other than said agent that blocks K-Cl cotransport in erythrocytes of the subject.

52. The kit of claim 49, further comprising, a container containing an anti-hemoglobinopathic agent other than said agent that blocks K-Cl cotransport n erythrocytes of the subject.

* * * * *